United States Patent [19]

Miwa et al.

[11] Patent Number: 4,512,195

[45] Date of Patent: Apr. 23, 1985

[54] ULTRASONIC LIVING BODY TISSUE CHARACTERIZATION METHOD

[75] Inventors: Hirohide Miwa, Kawasaki; Mitsuhiro Ueda, Tokyo, both of Japan

[73] Assignee: Fujitsu Limited, Kawasaki, Japan

[21] Appl. No.: 516,555

[22] Filed: Jul. 25, 1983

[30] Foreign Application Priority Data

Jul. 26, 1982 [JP] Japan .................... 57-129902

[51] Int. Cl.³ ............................................ G01N 29/00
[52] U.S. Cl. ........................................ 73/602; 128/660
[58] Field of Search ................. 73/602, 614, 620, 629, 73/599; 128/660; 364/485, 484, 576, 578, 582

[56] References Cited

U.S. PATENT DOCUMENTS

| | | | |
|---|---|---|---|
| 4,414,850 | 11/1983 | Miwa et al. | 73/602 |
| 4,452,082 | 6/1984 | Miwa | 73/599 |
| 4,470,303 | 9/1984 | O'Donnell | 73/602 |

*Primary Examiner*—Stephen A. Kreitman
*Attorney, Agent, or Firm*—Staas & Halsey

[57] ABSTRACT

This invention relates to a reflection type ultrasonic living body tissue characterization method obtaining highly accurate measuring result. The reflected ultrasonic wave power from the tissue to be measured is measured for respective frequency ranges. Then, it is normalized by the result of measuring the reflected ultrasonic wave power using a standard reflector placed in the equivalent region in non-attenuative medium to measure the tissue transfer function. Thereby, the characteristic of the measuring system can be eliminated. Moreover, unknown values not dependent on frequency are eliminated by normalizing the values measured at other frequencies with the value measured at a particular frequency. In addition, the corresponding transfer function of the tissue model is described with a product of an exponential function. Dividing the measured tissue transfer function with the non-exponential function and taking the logarithm makes the regression calculation of the measured function to the model function easier. Thereafter, various parameters indicating the tissue characteristic are obtained by regression calculations.

3 Claims, 6 Drawing Figures

ULTRASONIC LIVING BODY TISSUE CHARACTERIZATION METHOD

FIELD OF THE INVENTION

This invention relates to a method of measuring various characteristic values such as the $\beta$ of a medium; the medium being, for example, living body tissue. In performing the measurement, an attenuation constant which is proportional to frequency (the proportional constant being $\beta$) and a reflection coefficient which is a function of frequency and determined by various living body tissue characteristic values are normally used. More specifically, the invention relates to a method of obtaining various characteristic values of the medium by regressing to the theoretical equation, experimental equation from measured power spectrum values.

It is experimentally known that an attenuation constant in transmission of an ultrasonic wave is proportional to frequency f, the proportional constant $\beta$, indicates a tissue characteristic. It is also experimentally known that a reflection coefficient is proportional to the nth power of the frequency of the ultrasonic waves, and that the exponent n indicates another tissue characteristic.

The inventors of this invention, Dr. Ueda et al. theoretically indicate that the reflection coefficient is expressed in the form of $$bf^n e^{-d/\Omega^2}$$

Here, b and d have values depending on the tissue.

When the reflection coefficient is expressed as a function of frequency f, as expained above, there is not any generally established method of obtaining a living body tissue characteristic from the profile of the power spectrum. Dr. Miwa et al., inventors of this invention, have presented a patent application disclosing a method for obtaining values of n and $\beta$ via an energy ratio method when the reflection coefficient is expressed as a function of the nth power of frequency f. (U.S. Ser. No. 372,547, now U.S. Pat. No. 4,452,082, U.S. Ser. No. 269,861, now U.S. Pat. No. 4,414,850.

This method is effective, but because attention is due to at least three narrow band energy effects, an error may be caused by local unevenness of the ultrasonic spectrum, known as scalloping. Accordingly, this method has the following disadvantages: calculations are necessary for different sets of three frequencies in the effective frequency band; and statistic averaging process must be performed on the set of obtained values for n and $\beta$. Thus, many calculations are required.

SUMMARY OF THE INVENTION

It is an object of this invention, when deriving a transfer function of a living body tissue from the received signal of reflected ultrasonic waves and a living body tissue characteristic, to provide:

1. A method of looking at a shape of a spectrum to avoid the effect of power discontinuities at the interface of tissue regions;
2. A method which assures easy regression from measured tissue transfer function to the tissue model function obtained from theory and experiments, the tissue model function being expressed as a product of an exponential function and a non-exponential function; and
3. A method where the parameters involved in the function are determined by such regression and living body tissue characteristic values are obtained.

In this invention, the frequency response spectrum of a living body tissue transfer function is normalized; the important factor of the spectrum being its shape, not its absolute value. Moreover, when using a function derived for a tissue model from theory or experiment is expressed as a product of an exponential function and a non-exponentional function, parameters relating to the living body tissue characteristic can be obtained by regressing the measured function obtained firstly by a logarithmic operation, and secondly dividing the measured tissue transfer function with the non-exponentional function.

DESCRIPTION OF THE PREFERRED EMBODIMENT OF THE INVENTION

Figure 1:
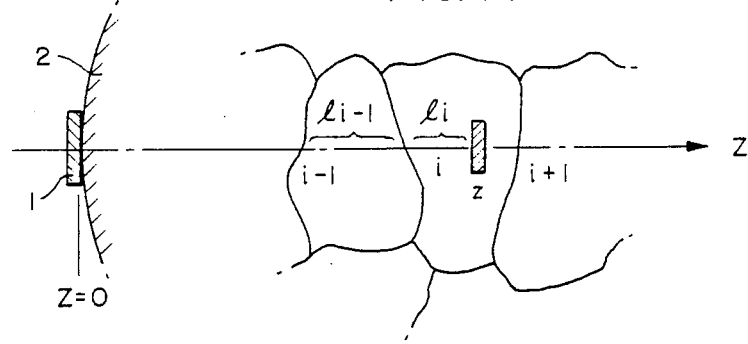
FIG. 1 is a schematic cross-sectional view of a living body tissue structure along the Z axis.

In FIG. 1 an ultrasonic wave pulse (center frequency fo, bandwidth $\Omega$) is transmitted from a transducer 1, through the surface of a body and into a deep region of a living body along a measuring line (i.e., in the direction Z). This pulse travels within the living body at the sound velocity C, and any reflected waves travel in the reverse direction at the sound velocity C. These reflected waves are then received by the transducer 1.

FIG. 1 schematically represents living body tissue. in FIG. 1 it is desired to measure the characteristics of the tissue at the depth z. The living body comprises i different kinds of tissue regions from the surface to the depth Z. The sound velocity along z is almost constant.

A sound pulse transmitted from the surface of living body 2, namely from the position of z=0, is attenuated as it travels deeper. For each region i, the attenuation constant is $\alpha i$. The attenuation constant is proportional to a frequency f in each region i. If a proportionality constant is chosen to be $\beta i$, $$\alpha i = ai + \beta i * f$$

Where ai is a constant and $\beta i$ is a parameter indicating a characteristic of the tissue at region i and is called an attenuation slope.

Associated with each region is an acoustic impedance due to macro tissue nature, and a power reflection coefficient r(f) due to random micro tissue structure, which is a function of frequency.

At the interface of each region, there is a large change in the acoustic specular. Additionally, the surface of each region is often specular. Consequently, when the pulse passes from the region i−1 to the i, a small amount of transmission loss occurs. The transmission loss, called transmissivity, is denoted by $\tau i$.

In the same way, the reflected waves from the depth z pass from the region i to region i−1 back towards the transducer 1. In this case the transmissivity is denoted as $\tau' i$. The $\tau i$ and $\tau' i$, are not considered to vary with frequency.

The transducer 1 begins to receive, shortly after transmitting an ultrasonic wave pulse, a continuous series of waves reflected from every region within the body. Since the reflected wave corresponding to the depth z is received at the time $t=2z/C$, the tissue characteristic at the depth z can be obtained by analyzing the reflected waveform during a certain narrow time around this time.

A power spectrum Er(f) of the received signal reflected from the depth z can be easily obtained using a known frequency analyzer such as FFT (Fast-Fourier transformer). This power spectrum Er(f) is given as the square of the product of a transfer function of the measuring system consisting of the frequency characteristic of transducer, the frequency characteristic of the beam convergence at the depth z, the transfer function of electronic circuit etc. and the transfer function of the living body tissue.

Here, a standard reflector is placed at the depth equivalent to z within non-attenuative homogeneous medium such as water and a power spectrum Eo(f) of the received wave is obtained. Here, Eo(f) is considered to be the square of the transfer function of the measuring system. When Er(f) is divided by Eo(f) the mormalized power spectrum results, and a square of the intrinsic transfer function of a living body tissue can be obtained. An actually measured transfer function of a living body tissue is indicated as R(f).

$$R(f) = Er/Eo \quad (1)$$

On the other hand, from the above explained tissue model, the measured transfer function R(f) must be expressed by the following equation.

$$\overline{R}(f) = k \cdot r(f) \cdot \left( \prod_{i=0}^{Z} \tau i \cdot \tau'i \right) \exp\left( -4 \sum_{i=0}^{Z} \beta i f l i \right) \quad (2)$$

r (f): power reflection coefficient
k: a constant not depending on f
i: path length within the region i
The symbols mean accumulation, namely $$\prod_{i=0}^{n} Ai = A_0 \times A_1 \times A_2 \ldots \times An.$$

$$\sum_{i=0}^{n} Ai = A_0 + A_1 + A_2 + \ldots + An$$

Explained hereunder is the method of obtaining a tissue characteristic by comparing R(f) of equation (1) and $\overline{R}$(f) of equation (2).

A transducer is only capable of obtaining a portion of R(f), within an effective bandwidth of the transducer. Therefore, the function R(f), covering a sufficiently wide frequency range must be obtained by utilizing a plurality of different frequency transducers and then combining these spectrums.

Because tissues actually comprise a collection of cells or muscle fibers, when actually measuring the power spectra, the measurements show local unevenness. This is because of the interference of reflected waves from closely but randomly located scatterers such as the cells fibers with the tissue, or tissue walls. The unevenness is called spectrum scalloping, and results in a large error in the measurement of the spectrum shape. In order to prevent such error, it is preferable to measure the power spectra of regions around to the measuring area; for example, the areas in front of, behind, to the right, left, above and below the desired region and/or to repeat the measurements several times. This special and/or temporal statistical averaging of the spectra can remove the unevenness.

Equation (2) can be normalized as indicated below with the R(fo) at a particular frequency fo (for example, a frequency fm which gives the maximum value of equation (1) etc.) in equation (2).

$$Q(f) = \overline{R(f)/R(fo)} = \frac{r(f)}{r(fo)} \times \frac{\exp[-(4\Sigma \beta i l i)f]}{\exp[(-4\Sigma \beta i l i)fo]} \quad (3)$$

In equation (3), the factors k, $\tau i$, $\tau'i$, are eliminated. Elimination of the unknown factors $\tau i$ and $\tau'i$, is a very important merit of this patent.

Since both fo and R(fo) can actually be measured, the measured power spectrum P(f) can be normalized by R(fo) as indicated below.

$$P(F) = R(F)/R(fo) \quad (4)$$

Therefore, the parameters involved in Q(f) can be determined by regressing P(f) to Q(f) without reference to $\tau i$ and $\tau'i$.

The power reflection function r(f) can be either an experimentally or a theoretically derived equation. For example, the following experimental equation can be used.

$$r(f) = a*F^n \quad (5)$$

Where a is a constant, and n is a constant depending on tissue. Or for example, r(f) can be expressed by the following theoretical equation by Ueda et al., $$r(f) = b \cdot b' \cdot f^4 \cdot \exp\left[ -\sigma z^2 \left( \frac{2\pi}{c} \right)^2 \cdot f^2 \right] \quad (6)$$

where,
b' is a function of frequency, the transducer size and its radius of curvature;
b is a constant depending on the macro nature of a heterogeneous tissue which is the same as the average microminiature structure of the tissue being measured;
$\sigma_z$ is a self-correlational distance factor, measured in the direction that the ultrasonic pulse traverses. Because each cell or fiber has a different size, this factor is equivalent to the means self-correlational length measured in the direction that the ultrasonic pulse traverses; and
c is the velocity of sound.

Equations (5) and (6) appear significantly different but, these equations provide almost identical results in a certain practically used frequency range such as the conventional range of (1~7 MHz).

When equation (5) or (6) is substituted into equation (3), $Q_5$ and $Q_6$ are respectively obtained as follows.

$$Q_5 = A_5 \cdot \exp[B_5(f)] \quad (7)$$

$$Q_6 = A_6 \cdot \exp[B_6(f)] \quad (8)$$

where, $A_5 = \dfrac{af^n}{\overline{R}(fo)}$, $B_5(f) = -4(\Sigma \beta i l i)f$ and -continued $$A_0 = \frac{bh'f^4}{R(f_0)}, \quad B_0(f) = -4(\Sigma\beta ili)f - \left(\frac{2\pi\sigma_z}{C}\right)^2 \cdot f^2.$$

As seen in equations (7) and (8), Q is a product of an exponential function of B(f) and an non-exponential function of A(f). When both equations are divided by the respective non-expenential functions the result can be expressed by the following logarithmic expressions.

$$\ln Q_5 / \frac{a}{R(f_0)} - n\ln f = -4(\Sigma\beta ili)f \quad (9)$$

$$\ln Q_6 / \frac{bh'}{R(f_0)} - nb'f = -4(\Sigma\beta ili)f - \left(\frac{2\pi\sigma_z}{C}\right)^2 f^2 \quad (10)$$

In equations (9) and (10), an actually measured P is substituted in place of $Q_5$ and $Q_6$ and the left sides are plotted as functions with frequency. Such plots are regressed to the right side functions with frequency by the means such as least the squared error method. Thereby, the parameters n, $\Sigma\beta ili$, $\sigma_z$ can be obtained.

Equation (9) contains the unknown value n on the left side but, a value of n which makes the right side to become a linear function of f, most closely can be determined numerically assuming a plurality of n.

A value of $\beta i$ for each i can be obtained from a difference of $$\sum_0^{z-\Delta z} \beta ili - \sum_0^z \beta ili$$

by obtaining a value of $$\sum_0^z \beta ili$$

at the depth z. When $\beta$ is expressed as a continuous function of z, its line integration is expressed as $$\int_0^z \beta dz.$$

Therefore, a value of $\beta(z)$ can be obtained by differentiation of the line integral or from the line integrations in all directions by the algorithm used in X-ray CT (Computer Tomography).

Figure 2:
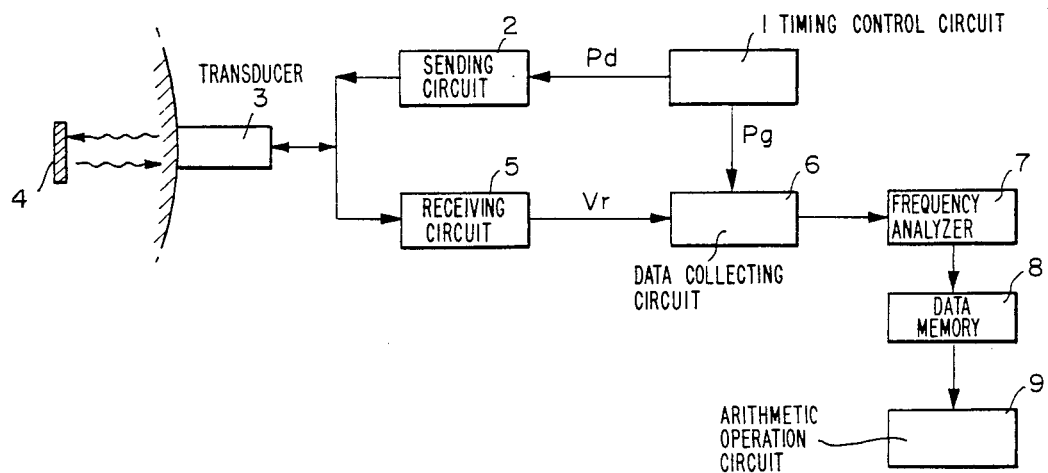
FIG. 2 is a block diagram of an embodiment of this invention.

Distribution of values for n, $\beta$ and $\sigma_z$ can be obtained along each measuring line, and a two dimensional distribution of n, $\beta$ and $\sigma_z$ can be obtained by scanning in a plane the measuring lines. Explained above is the principle of this invention. In actual implementation of this invention, time gating of echo signal corresponding to the sampling points at a certain depth z in a body is a well known technology in Doppler measurement. The gated waveforms are Fourier-analyzed by, for example, the DFT (Digital Fourier Transform) which is an easy means for obtaining the power spectrum of the gated waveforms. The processing of the spectrum to obtain the tissue characteristics can be executed by a computer or by specially constructed computing hardware. An outline of an illustrative system will be explained with reference to FIG. 2.

Figure 3:
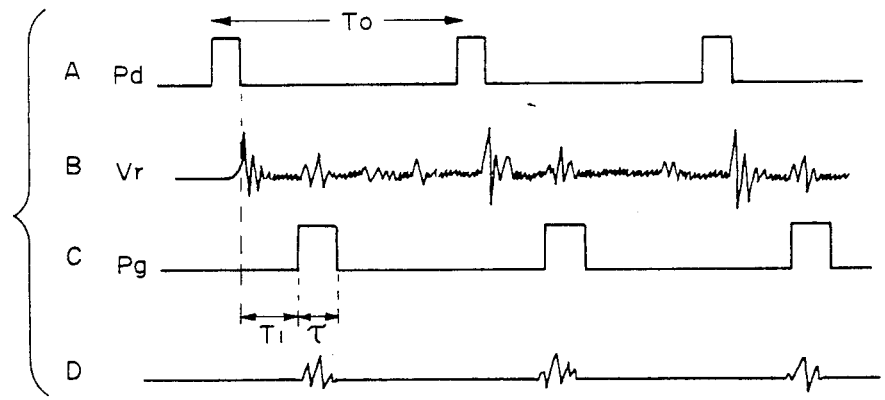
FIG. 3 illustrates waveforms at respective points of FIG. 2.

An ultrasonic transmitter synchronizing signal Pd, shown in FIG. 3 (A) is transmitted to a driving circuit 2, from a timing control circuit 1. A transducer 3, is driven by a pulse having a sufficient power necessary for the transducer to transmit an ultrasonic wave. Thereby an ultrasonic wave is transmitted into living body tissues (or into a water containing a standard reflector 4).

A reflected wave from the living body tissue (or from the standard reflector 4), is received by the transducer 3. This reflected wave is then amplified to an adequate level by a reciving circuit 5. The amplified signal is then sent to a data collecting circuit 6 as the received signal Vr shown in FIG. 3 (B).

The timing control circuit 1 sends a gate pulse Pg, shown in FIG. 3(C), to the data collecting circuit 6, delayed by the time T1 from Pd. The delay corresponding to a distance from the surface of the transducer to the reflecting area to be measured; thus, the reflected signal from the desired measuring region is collected as the data.

The width $\tau$ of Pg is determined corresponding to the range of depths to be measured. The data collected corresponds, for example, to the waveform shown in FIG. 3(D).

Figure 4A:
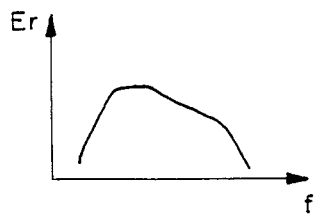
FIGS. 4a–c illustrates relation of frequency characteristics.
Figure 4B:
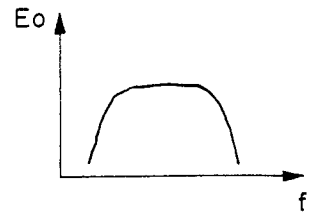

The collected data is sent to a frequency analyzer 7 and a result of the frequency analysis is sent to a data memory 8. The results of frequency analysis are the reflected wave spectrum from a living body tissue as shown in, for example, FIG. 4(A), and the reflected wave spectrum from the standard reflector as shown in FIG. 4(B).

Figure 4C:
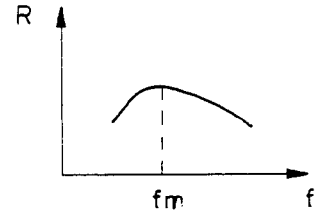

An arithmetic operation circuit 9 performs various calculations as described above using the results of the frequency analysis stored in the data memory 8. More specifically, a spectrum such a shown in FIG. 4(A) is divided by a spectrum such as shown in FIG. 4(B). Thereby a tissue transfer function R(f) (corresponding to equation (1)) shown in FIG. 4(C) is obtained. Thus, the frequency $f_m$ at which equation (3) is a maximum can be obtained, and moreover the left sides of the equations (9) and (10) can be calculated. Thereafter, regression calculations are carried out and values of n, $\Sigma\beta ili$ and $\sigma_z$ are determined. A values of $\beta i$ can also be obtained from the calculated value of $\Sigma\beta ili$ at each depth z.

The arithmetic operation circuit 9 may take any kind of structure so long as it can realize the above calculations. For example, a micro-computer consisting of a microprocessor, RAM, ROM, I/O port etc. may be used.

The present invention achieves the following results:
1. The effect of the measuring system can be eliminated by extracting a living body tissue transfer function by normalizing the spectrum with the one of a standard reflector, and the effect of discontinuous transmission can be eliminated by normalizing again the tissue transfer function with its value at a certain frequency;
2. Regression calculations can be realized easily by dividing the measured tissue transfer function with a non-exponential portion of the tissue model function and then rearranging the expression using logarithmic operators; and
3. The tissue characteristic can be obtained from the parameters thus obtained.

We claim:
1. An ultrasonic living body tissue characterization method wherein an ultrasonic wave pulse is transmitted by a measuring system into a living body, the reflected signals are received by the measuring system and a living body tissue characteristic is measured by analysing said received signals, said method comprising the steps of:
  (a) analyzing the frequency of signals reflected from the region to be measured to obtain the power spectrum of said reflected signals, Er(f);
  (b) obtaining the power spectrum Eo(f) of the measuring system by using a standard reflector positioned in the region equivalent to be measured in a non-attenuative medium;
  (c) normalizing the power spectrum Er(f) obtained in step (a) with the power spectrum Eo(f) to obtain the transfer function R(f) of a living body tissue, at the region to be measured;
  (d) obtaining the transfer function R(f) at a particular frequency fo;
  (e) obtaining P(f) by normalizing R(f) with R(fo) at the particular frequency fo;
  (f) obtaining P(f)/A(f) by dividing P(f) obtained in step (e) with A(f), utilizing the fact that the function Q(f), which is the transfer function R(f) of a living tissue model, normalized with its specific value at fo is expressed in the form of $$Q(f) = A(f) \cdot e^{B(f)},$$

(g) expressing the function obtained in step (f) using logarithmic operators; and
  (h) obtaining the optimum values of parameters of the functions A(f) and B(f) using regression processing such that the function obtained in step g is considered to be equal to the function B(f).

2. The ultrasonic living body tissue characterization method according to claim 1, wherein A(f) in the step (f) is expressed by an equation which is proportional to power n (n is a constant indicating a living body tissue characteristic) of the frequency f, B(f) is indicated by a linear function of frequency f, and a linear coefficient of frequency f is related to the line integration of the frequency slope (attenuation slope) of attenuation constant.

3. The ultrasonic living body tissue characterization method according to claim 1, wherein B(f) in the step (f) is expressed by the quadratic equation of frequency f, and the coefficients of constant, linear item and quadratic expression item are respectively the amounts in relation to average micro-miniature structure, line integration of attenuation slope and self-correlation distance in the scanning direction.

* * * * *

UNITED STATES PATENT AND TRADEMARK OFFICE
CERTIFICATE OF CORRECTION

PATENT NO. : 4,512,195
DATED : April 23, 1985
INVENTOR(S) : Hirohide Miwa et al

It is certified that error appears in the above-identified patent and that said Letters Patent is hereby corrected as shown below:

Column 3, line 42, italicized "l" should preceed "i" (first occurrence).

Column 4, line 40, "$\overline{\sigma z}^2$" should be --$\sigma_z^2$--.

Column 5, line 45, "$o^zBdz$" should be --$\int_o^z Bdz$--.

Column 6, line 43 and 44, the "l" in $\beta$ili should be italicized.

Column 8, line 1, "F" should be --f--.

Signed and Sealed this

Twenty-ninth Day of October 1985

[SEAL]

Attest:

DONALD J. QUIGG

Attesting Officer

Commissioner of Patents and Trademarks—Designate